(12) United States Patent
Johnson et al.

(10) Patent No.: US 7,412,890 B1
(45) Date of Patent: Aug. 19, 2008

(54) METHODS AND APPARATUS FOR DETECTING CRACKS IN WELDS

(75) Inventors: Paul Johnson, Huntersville, NC (US); David Galbally, San Jose, CA (US); Walter Anthony Mitchell, III, Huntersville, NC (US); Trevor James Davis, Charlotte, NC (US)

(73) Assignee: General Electric Company, Schenectady, NY (US)

( * ) Notice: Subject to any disclaimer, the term of this patent is extended or adjusted under 35 U.S.C. 154(b) by 54 days.

(21) Appl. No.: 10/750,417

(22) Filed: Dec. 31, 2003

(51) Int. Cl.
G01N 29/04 (2006.01)

(52) U.S. Cl. .................. 73/618; 622/625; 622/644

(58) Field of Classification Search ............ 73/618, 73/622, 625, 602, 865.8, 850, 640, 599, 822; 376/249, 252; 228/104; 600/445, 462
See application file for complete search history.

(56) References Cited

U.S. PATENT DOCUMENTS

| | | | |
|---|---|---|---|
| 3,202,218 A * | 8/1965 | Watts et al. ............... 166/356 |
| 3,616,684 A * | 11/1971 | Nusbickel, Jr. ............ 73/635 |
| 3,938,372 A * | 2/1976 | Sproule .................. 73/633 |
| 3,988,922 A * | 11/1976 | Clark et al. ............. 376/249 |
| 4,368,644 A * | 1/1983 | Wentzell et al. ............ 73/634 |
| 4,455,872 A * | 6/1984 | Kossoff et al. ............. 73/618 |
| 4,641,532 A * | 2/1987 | Rohrer .................. 73/637 |
| 4,785,816 A * | 11/1988 | Dow et al. ............... 600/446 |
| 4,966,746 A | 10/1990 | Richardson et al. |
| 5,009,105 A * | 4/1991 | Richardson et al. .......... 73/621 |
| 5,156,803 A | 10/1992 | Engding et al. |
| 5,228,343 A * | 7/1993 | Schoenen et al. ............ 73/644 |
| 5,377,237 A | 12/1994 | Richardson et al. |
| 5,460,045 A | 10/1995 | Clark et al. |
| 5,460,179 A * | 10/1995 | Okunuki et al. ............ 600/444 |
| 5,568,527 A | 10/1996 | Richardson et al. |
| 5,571,968 A * | 11/1996 | Buckley .................. 73/623 |
| 5,784,425 A | 7/1998 | Morlan |
| 6,076,407 A | 6/2000 | Levesque et al. |
| 6,120,452 A * | 9/2000 | Barthe et al. ............. 600/459 |
| 6,169,776 B1 | 1/2001 | Collins |
| 6,332,011 B1 | 12/2001 | Johnson |
| 6,865,243 B2 * | 3/2005 | Paillaman et al. .......... 376/245 |
| 6,886,407 B1 * | 5/2005 | Fredenberg ............... 73/622 |
| 6,904,817 B2 * | 6/2005 | Davis et al. .............. 73/865.8 |
| 7,134,352 B2 * | 11/2006 | Davis et al. .............. 73/865.8 |
| 2005/0124889 A1 * | 6/2005 | Flesch ................... 600/445 |
| 2005/0288587 A1 * | 12/2005 | Roh et al. ............... 600/445 |

* cited by examiner

Primary Examiner—Hezron E. Williams
Assistant Examiner—Jacques M. Saint-Surin
(74) Attorney, Agent, or Firm—Armstrong Teasdale LLP

(57) ABSTRACT

A method of inspecting a portion of a weld between at least two materials includes mounting at least one ultrasonic phased array probe including at least one transducer having a plurality of elements within a housing containing a liquid therein, attaching the housing adjacent to an outer surface of the portion of the weld such that the liquid is adjacent to the outer surface of the portion of the weld, and scanning the weld with the at least one ultrasonic phased array probe.

16 Claims, 5 Drawing Sheets

METHODS AND APPARATUS FOR DETECTING CRACKS IN WELDS

BACKGROUND OF THE INVENTION

This invention relates generally to inspection of nuclear reactors, and more particularly to ultrasonic examination of welds within a nuclear reactor pressure vessel (RPV).

A typical boiling water reactor (BWR) includes a RPV containing a nuclear fuel core immersed in circulating coolant water which removes heat from the nuclear fuel. The water is boiled to generate steam for driving a steam turbine-generator for generating electric power. The steam is then condensed and the water is returned to the pressure vessel in a closed loop system. Piping circuits carry steam to the turbines and carry re-circulated water or feed-water back to the RPV that contains the nuclear fuel. BWRs have numerous piping systems, and such piping systems are utilized, for example, to transport water throughout the RPV. For example, core spray piping is used to deliver water from outside the RPV to core spargers inside the RPV and to cool the core. Typically, the core spray piping is coupled to a thermal sleeve that is welded to a RPV nozzle and a safe-end is welded to the nozzle.

Stress corrosion cracking (SCC) is a known phenomenon that may occur in reactor components, such as structural members, piping, fasteners, and welds. The reactor components are subject to a variety of stresses associated with, for example, differences in thermal expansion, the operating pressure needed for the containment of the reactor cooling water, and other sources such as residual stresses from welding, cold working and other inhomogeneous metal treatments. In addition, water chemistry, welding, heat treatment and radiation can increase the susceptibility of metal in a component to SCC. Reactor internal piping, such as thermal sleeves and core spray lines, occasionally require replacement as a result of SCC, the replacement may require welding a new pipe member onto an old pipe member.

Some known methods of inspecting welds for SCC utilize a phased array probe. Known phased arrays include a group of transducer elements used together with relative time, or phase shifts between the elements. The combined elements act as a single instrument that can be steered to distinct points in space. Typically, known methods average ten hours to scan a thirty-centimeter weld.

BRIEF DESCRIPTION OF THE INVENTION

In one aspect, a method of inspecting a portion of a weld between at least two materials is provided. The method includes mounting at least one ultrasonic phased array probe including at least one transducer having a plurality of elements within a housing containing a liquid therein, attaching the housing adjacent to an outer surface of the portion of the weld such that the liquid is adjacent to the outer surface of the portion of the weld, and scanning the weld with at least one ultrasonic phased array probe.

In another aspect, an apparatus configured to inspect a portion of a weld between at least two materials is provided. The apparatus includes a housing containing liquid and at least one ultrasonic phased array probe mounted within said housing.

In a further aspect, a method of inspecting a portion of at least two pipes coupled by a weld within a nuclear reactor pressure vehicle is provided. The method includes mounting at least one ultrasonic phased array probe within a housing partially containing a liquid therein, wherein at least one ultrasonic phased array probe includes at least one transducer having a plurality of elements, and wherein the housing is configured to position at least one ultrasonic phased array probe at a predetermined location on the weld, attaching the housing adjacent to an outer surface of the at least two pipes such that the portion of the weld to be inspected is positioned therein and the liquid is adjacent to the outer surface of the weld, and scanning the portion of the weld with at least one ultrasonic phased array probe, wherein the probe emits a steerable ultrasonic beam.

DETAILED DESCRIPTION OF THE INVENTION

Figure 1:
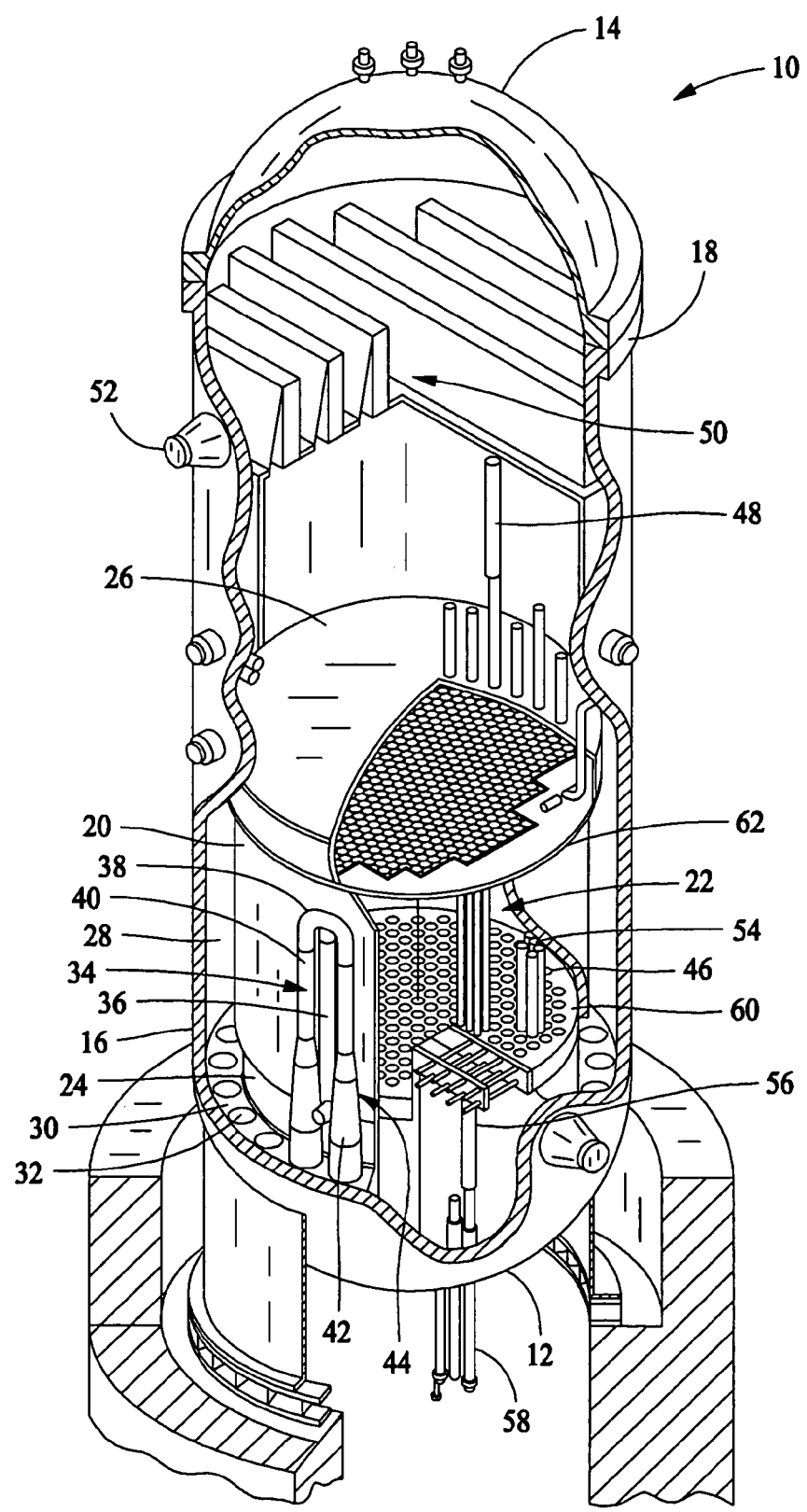
FIG. 1 is a sectional view, with parts cut away, of a boiling water nuclear reactor pressure vessel.

FIG. 1 is a sectional view, with parts cut away, of a boiling water nuclear reactor pressure vessel (RPV) 10. RPV 10 has a generally cylindrical shape and is closed at one end by a bottom head 12 and at its other end by a removable top head 14. A side wall 16 extends from bottom head 12 to top head 14. Side wall 16 includes a top flange 18. Top head 14 is attached to top flange 18. A cylindrically shaped core shroud 20 surrounds a reactor core 22. Shroud 20 is supported at one end by a shroud support 24 and includes a removable shroud head 26 at the other end. An annulus 28 is formed between shroud 20 and side wall 16. A pump deck 30, which has a ring shape, extends between shroud support 24 and RPV side wall 16. Pump deck 30 includes a plurality of circular openings 32, with each opening housing a jet pump 34. Jet pumps 34 are circumferentially distributed around core shroud 20. An inlet riser pipe 36 is coupled to two jet pumps 34 by a transition assembly 38. Each jet pump 34 includes an inlet mixer 40, and a diffuser 42. Inlet riser 36 and two connected jet pumps 34 form a jet pump assembly 44.

Heat is generated within core 22, which includes fuel bundles 46 of fissionable material. Water circulated up through core 22 is at least partially converted to steam. Steam separators 48 separate steam from water, which is re-circulated. Steam dryers 50 remove residual water from the steam. The steam exits RPV 10 through a steam outlet 52 near vessel top head 14.

The amount of heat generated in core 22 is regulated by inserting and withdrawing control rods 54 of neutron absorbing material, such as for example, hafnium. To the extent that control rod 54 is inserted into fuel bundle 46, it absorbs neutrons that would otherwise be available to promote the chain reaction which generates heat in core 22. Control rod guide tubes 56 maintain the vertical motion of control rods 54 during insertion and withdrawal. Control rod drives 58 effect the insertion and withdrawal of control rods 54. Control rod drives 58 extend through bottom head 12.

Fuel bundles 46 are aligned by a core plate 60 located at the base of core 22. A top guide 62 aligns fuel bundles 46 as they are lowered into core 22. Core plate 60 and top guide 62 are supported by core shroud 20.

Figure 2:
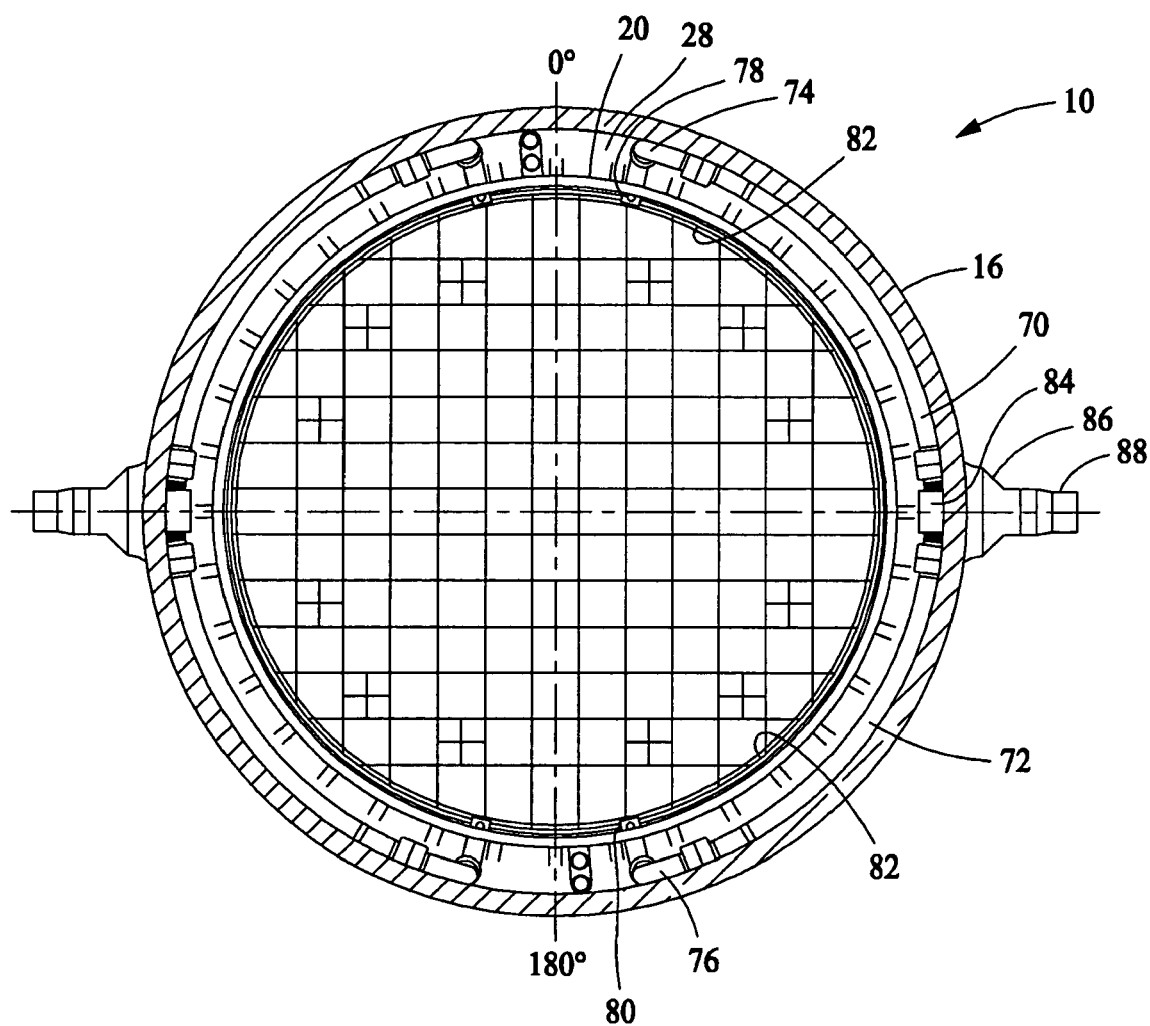
FIG. 2 is a top sectional view of the boiling water nuclear reactor pressure vessel shown in FIG. 1.

FIG. 2 is a top sectional view of RPV 10 including annulus 28 formed between vessel wall 16 and shroud 20. Space inside annulus 28 is limited with most reactor support piping located inside annulus 28. Cooling water is delivered to the reactor core during a loss of coolant accident through core spray distribution header pipes 70 and 72 which are connected to downcomer pipes 74 and 76 respectively. Downcomer pipes 74 and 76 are connected to shroud 20 through lower T-boxes 78 and 80 respectively, which are attached to shroud 20 and internal spargers 82. Distribution header pipes 70 and 72 diverge from an upper T-box assembly 84. Particularly, T-box assembly 84 is coupled to a core spray nozzle 86 by a thermal sleeve (shown in FIG. 3). Core spray nozzle 86 is coupled to a safe-end 88.

Figure 3:
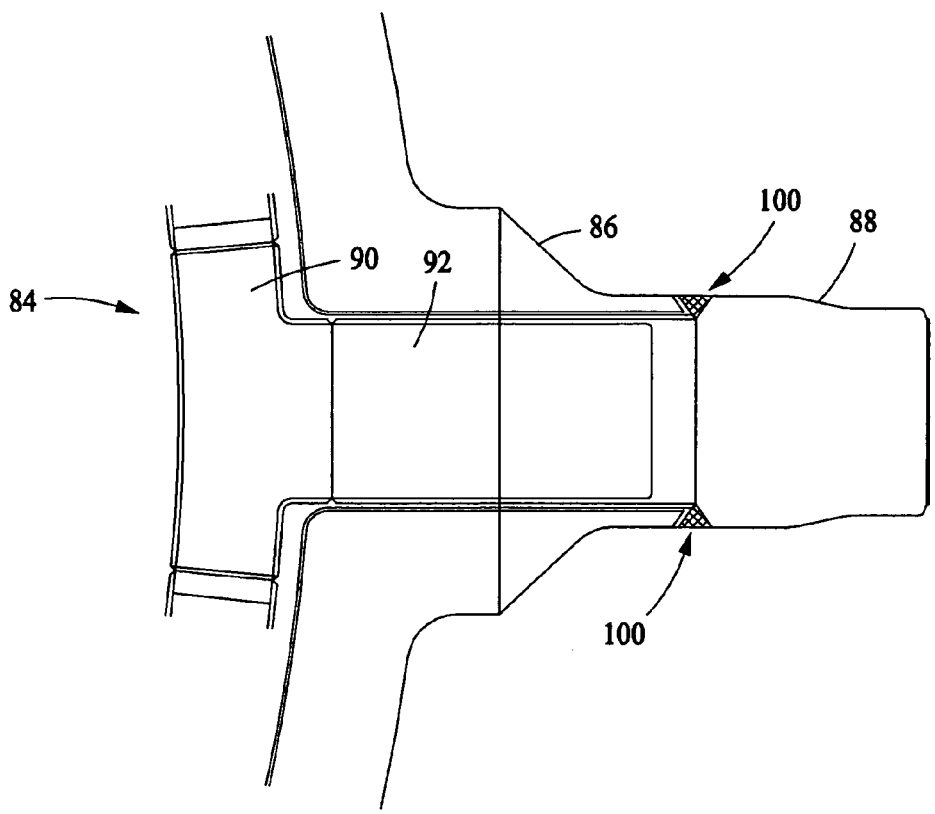
FIG. 3 is a sectional view, with parts cut away, of a T-box assembly and nozzle/safe end configuration shown in FIG. 2.

FIG. 3 is a side sectional view with parts cut away of T-box assembly 84. T-box assembly 84 includes a T-box housing 90 that is welded to thermal sleeve 92 inside core spray nozzle 86. Core spray nozzle 86 is coupled to safe-end 88 by a weld 100, sometimes referred to as a core spray safe-end-to-nozzle (SE-Noz) weld.

Figure 4:
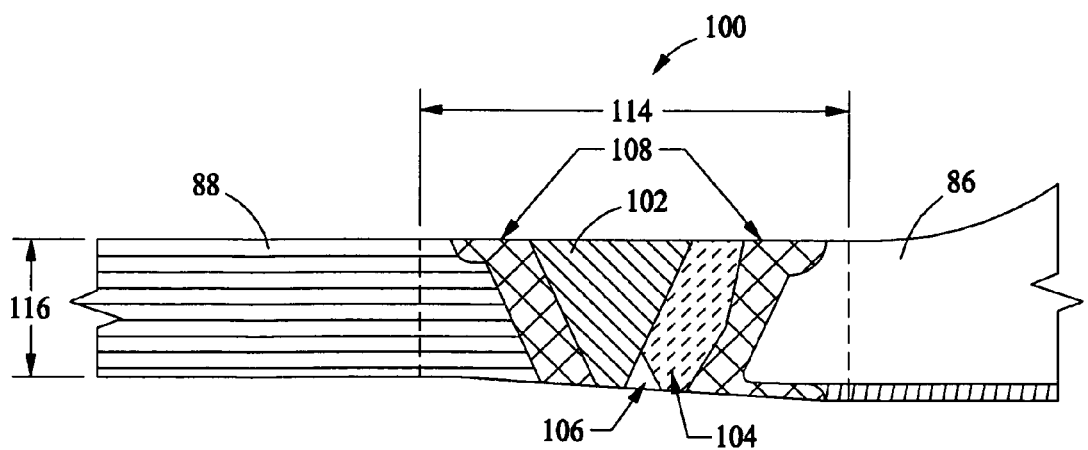
FIG. 4 is a side view of a SE-Noz weld shown in FIG. 3.

FIG. 4 is a sectional side view with parts cut away of SE-Noz weld 100 positioned between safe-end 88 and core spray nozzle 86. In another embodiment, weld 100 is a recirculation nozzle-to-safe-end weld. In yet another embodiment, weld 100 is a safe-end thermal sleeve weld. Weld 100 is a circumferential weld. In the exemplary embodiment, SE-Noz weld 100 couples a new safe-end 88 manufactured from SS304 to an existing core spray nozzle 86 manufactured from SA508. In one embodiment, weld 100 is a dissimilar metal weld. In another embodiment, weld 100 contains Inconel® 600 series base materials, alloy 82 and 182 weld butter. Inconel® is a registered trademark of Special Materials, Huntington, W. Va. In the exemplary embodiment, weld 100 includes a new Inconel® weld 102, an old Inconel® weld 104, and a portion of an old Inconel® safe-end weld 106 all positioned between an Inconel® butter 108. Weld 100 has a weld width 114 and a weld thickness 116. Weld width 114 is between approximately fifteen centimeters and seventy centimeters. Weld thickness 116 is between approximately 1.75 centimeters and 6.25 centimeters.

The weld location, material, width 114, and thickness 116 described above are examples of weld 100. It can be appreciated that the instant invention may apply to any welds between similar or dissimilar materials, as well as weld materials that are similar or dissimilar to the materials being coupled. Additionally, the application applies to welds of varying thicknesses, widths, and locations.

Figure 5:
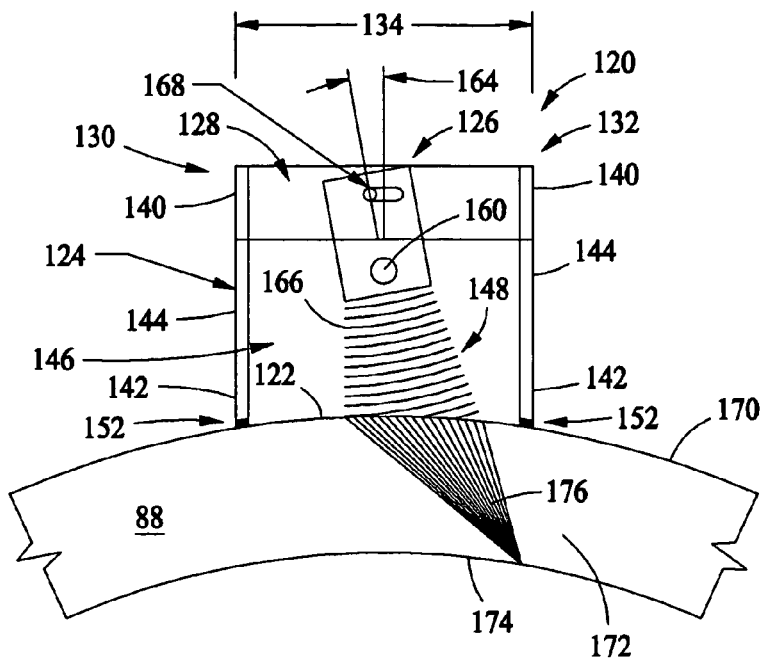
FIG. 5 is a side view of an ultrasonic phased array assembly mounted on the surface of the weld shown in FIG. 4 and shows a cross-sectional view of the pipe in accordance with an embodiment of the present invention.

FIG. 5 is a side view of a phased array probe assembly 120 adjacent an outer surface 122 of weld 100 in accordance with an exemplary embodiment of the present invention. Probe assembly 120 includes a fixture or housing 124 configured to receive and mount a probe 126 therein. Housing 124 is fabricated from a known water-impermeable material according to known techniques. Housing 124 is substantially rectangular shaped and surrounds a cavity 128. Housing 124 includes a first wall 130, a second wall 132, and a pair of side walls (not shown) extending substantially perpendicular to and adjacent first wall 130 and second wall 132. Housing 124 has a width 134 and length (not shown). Additionally, housing width 134 is sized greater than weld width 114 (shown in FIG. 4).

Each of first wall 130, second wall 132, and the pair of side walls include a top end 140, a bottom end 142, and a body 144 extending therebetween. Housing top end 140 is open such that a liquid 146 may be positioned within housing cavity 128. Housing bottom end 142 is open such that an ultrasonic beam 148 is not obstructed during emission toward weld 100. Additionally, each housing bottom end 142 is shaped to cooperate with the geometry of the item or material being inspected. In one embodiment, bottom end 142 is substantially concave. In an alternative embodiment, bottom end 142 is substantially flat.

Housing cavity 128 is filled with liquid 146. In one embodiment, liquid 146 is water. In another embodiment, liquid 146 is a combination of liquids that facilitate the transmission and reception of ultrasonic sound beams 148.

Housing 128 is releasably attached to outer surface 122 by a seal 152. Housing 128 can be incrementally moved axially or circumferentially along outer surface 122. In one embodiment, housing 128 is continuously moved axially or circumferentially along surface 122 in predetermined increments. Seal 152 is water-tight such that liquid 146 cannot drain out of housing cavity 128. In one embodiment, seal 152 is an elastomer. In another embodiment, seal 152 is a material selected from the group including rubber, silicone, and butyl.

Figure 6:
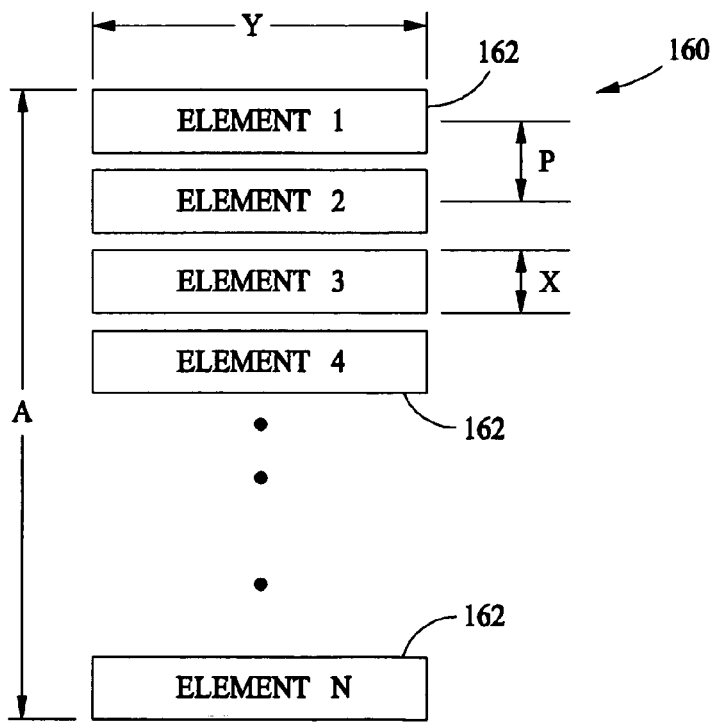
FIG. 6 is a schematic top view of an ultrasonic phased array transducer shown in FIG. 5.

FIG. 6 is a schematic top view of an array transducer 160 shown in FIG. 5. Referring to Figures and 5 and 6, probe 126 contains at least one array transducer 160 having a plurality of elements 162 that emit ultrasonic beam 148. An important aspect of probe 126 usage is the ability to dynamically synthesize ultrasonic beam 148 and create a "Virtual Probe" of any angle within the overall beam spread of an individual element. During operation, beam 148 is created by sequentially firing each element 162 to create a wave front 166 following a desired angle 164. Angle 164 is selected and set up electronically by control instrumentation (not shown) which controls an actuator 168, and can if necessary be changed pulse by pulse. This "Virtual Probe" can also be "swept" through weld 100 by firing groups of elements in a large array. This effect can be used to dynamically focus or "electrically steer" ultrasonic beam 148 by selecting the probe firing order and pulse delays. This can be changed on a pulse by pulse basis to effectively "sweep" a focal point through weld 100. Beam steering and dynamic focusing can be combined to enable resultant beam 148 to be both focused and angled in predetermined increments. Ultrasonic phased array probes 126 are commercially available from Krautkramer Ultrasonic Systems Group of Agfa NDT, Inc., Lewistown, Pa.

Referring to FIG. 6, the basic parameters of transducer 160 are defined as frequency, aperture A, element size X, element width Y, pitch P, and number of elements 162. A suitable frequency is 1.0 to 5.0 MHz for the material type and thickness 116 of weld 100. However, other transducer frequencies can be used for pipes and pipe welds manufactured from other materials.

Element pitch P is determined by calculating the acoustic aperture A needed to focus beam 148 at the required sound path and dividing this value by the total number of elements 162 and the amount of steering needed to create the desired angles. The size X of elements 162 is set as the maximum possible pitch. The width Y of elements 162 is determined by calculating the effective diameter for a near field of fifteen centimeters to give the smallest beam profile in the y-plane. The physical restrictions of the scanning surface must also be considered in determining the basic parameter values of probe 126.

Figure 7:
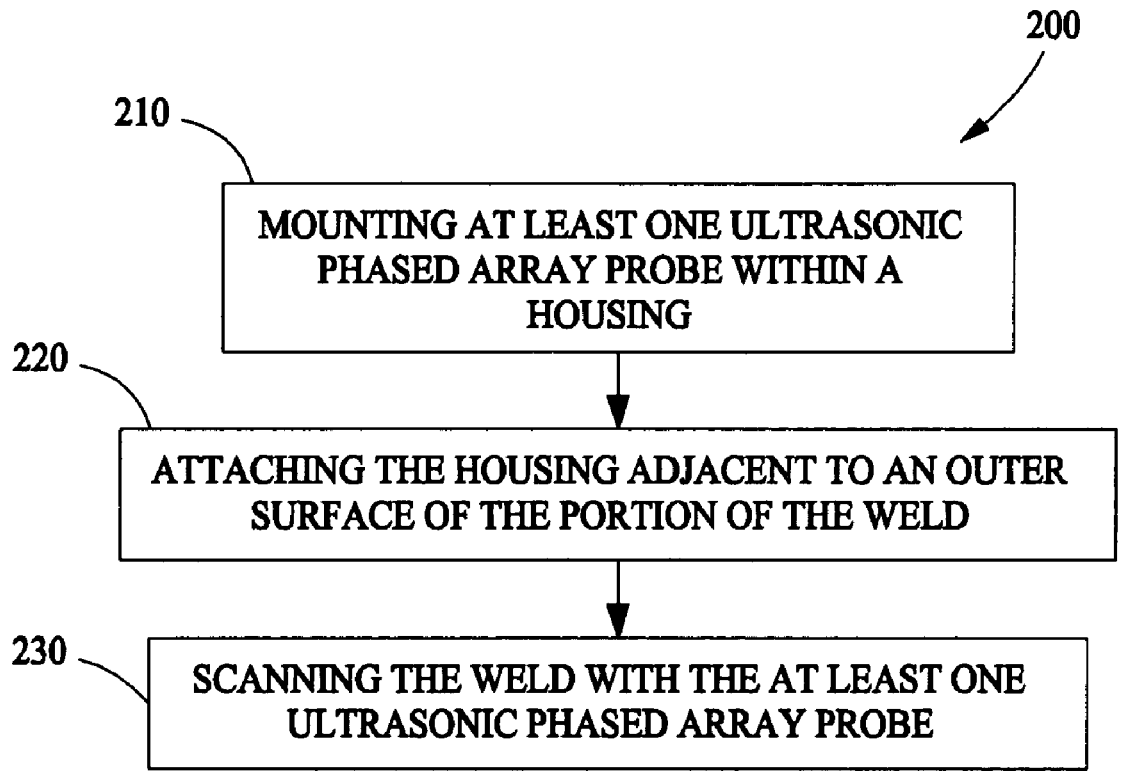
FIG. 7 is a flow chart of a method of inspecting a portion of a weld between at least two dissimilar materials in accordance with an embodiment of the present invention.

FIG. 7 is a flowchart depicting an exemplary embodiment of a method 200 of inspecting a portion of weld 100 that includes mounting 210 at least one ultrasonic phased array probe 126 within housing 124 containing liquid 146 therein such that at least a portion of probe 126 contacts liquid 146. Probe 126 is configured to rotate about a plurality of angles 164 using actuator 168.

Attaching 220 housing 124 adjacent to outer surface 122 of weld 100 facilitates inspection of weld 100. Liquid 146 is positioned adjacent outer surface 122 of weld 100 such that a water-tight seal 152 exists between housing 124 and surface 122. In one embodiment, seal 152 is removably attached. In another embodiment, seal 52 is fixedly attached. Housing 124 is configured to be moveably attached to surface 122 such that housing 124 may be rotated circumferentially about weld 100 incrementally.

Probe 126 is configured to scan weld 100 between at least two dissimilar materials of nozzle 86 and safe-end 88. In another embodiment, probe 126 is configured to scan weld 100 between at least two similar materials. Particularly, attaching 220 housing 124 to outer surface 122 and scanning 230 weld 100 with probe 126, facilitates an ultrasonic examination of materials of nozzle 86 and safe-end 88, for example, an outer surface 170, a body 172, and an inner surface 174, as well as weld 100. As shown in FIG. 5, the volume 176 of beam 148 that is examined includes weld 100 and nozzle 86 extending from outer surface 170 towards inner surface 174. Just as probe 126 can be oriented in a plurality of angles 164, as discussed above, beam 148 can be oriented or steered in plurality of angles 164. In one embodiment, beam 148 can be steered along a substantially axial path across weld 100 in a linear path perpendicular to the orientation of weld 100. In another embodiment, beam 148 can be steered along a substantially axial path across weld 100 in a linear path perpendicular to the orientation of weld 100 in predetermined increments. In yet another embodiment, beam 148 can be steered along a substantially circular path across weld 100.

The above described method 200 of inspecting a portion of weld 100 between at least two dissimilar materials of nozzle 86 and safe-end 88 permits the inspection with less personnel, with less exposure, and with less time. Additionally, the inspection results in a more complete and more reliable examination of welds between dissimilar or similar materials.

While the invention has been described in terms of various specific embodiments, those skilled in the art will recognize that the invention can be practiced with modification within the spirit and scope of the claims.

What is claimed is:

1. A method of inspecting a portion of a weld between at least two materials, said method comprising:
   pivotably mounting at least one ultrasonic phased array probe within a probe housing, the probe housing comprising a plurality of sides, an open top end and an open bottom end, the plurality of sides defining a housing cavity, each ultrasonic phased array probe comprising at least one transducer having a plurality of elements, the at least one ultrasonic phased array probe pivotable within the probe housing;
   attaching the probe housing to an outer surface of the portion of the weld so that the outer surface of the portion of the weld acts as a bottom end of the housing cavity;
   filling at least a portion of the housing cavity with a liquid so that the liquid is in contact with the outer surface of the portion of the weld; and
   scanning the weld with the at least one ultrasonic phased array probe.

2. A method in accordance with claim 1 wherein the weld is between at least two similar materials.

3. A method in accordance with claim 1 wherein the weld is between at least two dissimilar materials.

4. A method in accordance with claim 1 wherein mounting at least one ultrasonic phased array probe within the probe housing further comprises rotating the at least one ultrasonic phased array probe within the probe housing about a plurality of angles using an actuator.

5. A method in accordance with claim 1 wherein mounting at least one ultrasonic phased array probe within the probe housing comprises positioning at least one ultrasonic phased array probe partially within the liquid and at a predetermined location along the weld.

6. A method in accordance with claim 1 wherein the probe housing comprises a seal attached to a bottom edge of the plurality of sides, and attaching the probe housing to the surface of the weld comprises releasably attaching the probe housing such that a water-tight seal exists between the housing and the surface of the portion of the weld, wherein the seal is an elastomer.

7. A method in accordance with claim 1 wherein scanning the weld with the at least one ultrasonic phased array probe comprises electrically steering at least one of the elements such that an ultrasonic beam is emitted at a plurality of steering angles.

8. A method in accordance with claim 7 wherein electrically steering at least one of the transducer elements comprises actuating and deactuating at least one of the transducer elements along a path in a predetermined order.

9. A method in accordance with claim 7 wherein electronically steering the emitted ultrasonic beam comprises actuating at least one of the elements along a substantially axial path across the portion of the weld in a linear path in predetermined increments from an outer surface toward an inner surface.

10. A method in accordance with claim 7 wherein electronically steering the emitted ultrasonic beam comprises actuating at least one of the elements along a substantially circular path across the portion of the weld from an outer surface toward an inner surface.

11. A method of inspecting a portion of at least two pipes coupled by a weld within a nuclear reactor pressure vehicle, said method comprising:
   pivotably mounting at least one ultrasonic phased array probe within a probe housing, the probe housing comprising a plurality of sides, an open top end and an open bottom end, the plurality of sides defining a housing cavity, the at least one ultrasonic phased array probe includes at least one transducer having a plurality of elements, and the probe housing is configured to position the at least one ultrasonic phased array probe at a predetermined location on the weld, the at least one ultrasonic phased array probe pivotable within the probe housing;
   attaching the probe housing to an outer surface of the at least two pipes such that the portion of the weld to be inspected is positioned therein, the outer surface of the of the at least two pipes acts as a bottom end of the housing cavity;
   filling at least a portion of the housing cavity with a liquid so that the liquid is in contact with the outer surface of the of the at least two pipes; and
   scanning the portion of the weld with the at least one ultrasonic phased array probe, wherein the probe emits a steerable ultrasonic beam.

12. A method in accordance with claim 11 wherein mounting at least one ultrasonic phased array probe within the probe housing further comprises rotating the at least one ultrasonic phased array probe within the probe housing about a plurality of angles using an actuator.

13. A method in accordance with claim 11 wherein the probe housing comprises a seal attached to a bottom edge of the plurality of sides, and attaching the probe housing to the surface of the at least two pipes comprises releasably attaching the probe housing such that a water-tight seal exists between the probe housing and the surface of the portion of the weld, wherein the seal is an elastomer.

14. A method in accordance with claim 11 wherein scanning the weld with the at least one ultrasonic phased array probe comprises electrically steering at least one of the transducer elements at a plurality of steering angles.

15. A method in accordance with claim 14 wherein electrically steering further comprises actuating and deactuating at least one of the transducer elements along a substantially axial path across the portion of the weld in a linear path in a predetermined order from an outer surface toward an inner surface.

16. A method in accordance with claim 14 wherein electrically steering further comprises actuating and deactuating at least one of the transducer elements along a substantially circular path across the portion of the weld from the outer surface toward the inner surface.

* * * * *